United States Patent [19]

Cox et al.

[11] Patent Number: 4,983,323

[45] Date of Patent: Jan. 8, 1991

[54] SURFACTANT COMPOSITIONS

[75] Inventors: Michael F. Cox; Peter A. Schwab; Dewey L. Smith, all of Ponca City, Okla.

[73] Assignee: Vista Chemical Company, Houston, Tex.

[21] Appl. No.: 337,065

[22] Filed: Apr. 12, 1989

[51] Int. Cl.[5] ........................ C11D 1/12; C11D 1/755; C07C 43/11; C07C 43/18

[52] U.S. Cl. .................................... 252/551; 252/532; 252/153; 252/DIG. 14; 252/DIG. 4; 568/618

[58] Field of Search ....... 252/532, 551, 153, DIG. 14, 252/DIG. 4; 568/618

[56] References Cited

U.S. PATENT DOCUMENTS

| | | | |
|---|---|---|---|
| 3,211,661 | 10/1965 | Smith | 252/153 |
| 3,565,939 | 2/1971 | Beiser | 252/551 |
| 3,781,003 | 1/1974 | Hunter | 252/551 |
| 4,028,280 | 6/1977 | Murata | 252/551 |

*Primary Examiner*—Paul Lieberman

*Assistant Examiner*—James M. Silbermann

*Attorney, Agent, or Firm*—Browning, Bushman, Anderson & Brookhart

[57] ABSTRACT

A composition for use in formulating detergents containing water, a neutral salt thixotrope and a water-soluble salt of an ether sulfate having the formula $$[R{-}(A_n){-}O{-}SO_3]_xM$$

wherein R is a hydrocarbon group containing from about 4 to about 30 carbon atoms, A is an oxyalkylene group selected from the group consisting of oxyethylene, oxypropylene, oxybutylene, oxytetramethylene and heteric and block mixtures thereof, n is an integer from 1 to 8 and M is a cation of a water-soluble salt, and wherein at least about 85% by weight of said ether sulfate has a number average oxyalkylene number of p-2 to p+3, wherein p represents the number of oxyalkylene groups of the most prevalent oxyalkylate species, and x is 1 or 2 depending on the valence of M.

7 Claims, No Drawings

SURFACTANT COMPOSITIONS

BACKGROUND OF THE INVENTION

1. Field of the Invention

The present invention relates to surfactant compositions and, more particularly, to surfactant compositions for use in formulating detergent products.

2. Description of the Background

Ether sulfates, most generally alkyl polyalkylene ether sulfates, i.e. sulfates of alkoxylated non-aromatic alcohols, are widely used surfactants and find particular utility in the preparation of detergents which are used, for example, in liquid cleaning agents, foam baths, shampoos, hand soaps, etc. In obtaining the ether sulfates, the nonaromatic alcohols, which generally range from 8 to 24 carbon atoms, particular 8 to 18 carbon atoms, are first alkoxylated with lower alkylene oxides, especially with ethylene oxide and/or propylene oxide, subsequently sulfated and then converted into the respective water-soluble salts.

It is known that aqueous solutions having a relatively low content of such ether sulfates, for example, containing about 10% by weight of the ether sulfate, exhibit the special property of being thickened or viscosified by the addition of neutral salts, such as NaCl or $Na_2SO_4$. This rheological property of ether sulfates is taken advantage of in formulating detergent products, such as the types mentioned above.

It is also known that non-ionic surfactants of the alkoxylated alcohol type exhibit different properties depending on the alkoxylation species present. For example, certain alkoxylation species provide much greater activity than others. As disclosed in U.S. Pat. Nos. 4,754,075 and 4,775,653, a narrow distribution of the alkoxylation species is more desirable in many surfactant applications. For example, U.S. Pat. Nos. 4,210,764; 4,223,164; 4,239,917; 4,254,287; 4,302,613 and 4,306,093 all disclose alkoxylates having a narrow molecular weight distribution and which exhibit better detergency than prior art products having a broader distribution. Such alkoxylates are commonly referred to as "peaked".

SUMMARY OF THE INVENTION

It is therefore an object of the present invention to provide a surfactant composition for use in formulating detergent products.

Another object of the present invention is to provide a viscosified surfactant composition.

The above and other objects of the present invention will become apparent from the drawings, the description given herein and the appended claims.

The composition of the present invention contains water, a neutral salt thixotrope in an amount necessary to achieve the desired amount of viscosity, and an effective amount of a water-soluble salt of an aryl, aralkyl or alkyl polyalkylene ether sulfate having the formula $$[R-(A)_nO-SO_3]_xM$$

wherein R is a hydrocarbon group containing from about 4 to about 30 carbon atoms, A is an oxyalkylene group selected from the group consisting of oxyethylene, oxypropylene, oxybutylene, oxytetramethylene and heteric and block mixtures thereof, n is an integer from 1 to 8 and M is a cation of a water-soluble salt, and wherein when the average of n is from 1 to 8, at least about 85% by weight of said ether sulfate has a number average oxyalkylene number of $p-2$ to $p+3$, wherein p represents the number of oxyalkyene groups of the most prevalent oxyalkylate species, and x is 1 or 2 depending on the valence of M.

DESCRIPTION OF THE PREFERRED EMBODIMENTS

The compositions of the present invention include three main ingredients, namely, water, a neutral salt thixotrope and an aryl, aralkyl or alkyl polyalkylene ether sulfate (ES).

The term "neutral salt thixotrope" refers to any number of inorganic, water-soluble salts which will thicken an aqueous solution of the ES salt. Non-limiting examples of such salts include the alkali metal halides, sulfates, nitrates; ammonium salts, such as ammonium halides, ammonium sulfate and the like. Especially preferred are salts such as sodium chloride and sodium sulfate because of their ready availabilty and low cost. The salt thixotrope will be present in the compositions in a viscosifying amount, i.e. an amount which will alter the rheological properties of the composition to the desired extent. For example, it is often desired that shampoos have a relatively high viscosity, while liquid hand washing detergents have a considerably lower viscosity. Generally speaking, the salt thixotrope will be present in the composition in an amount of from about 1 to about 10% by weight, depending upon whether it is desired to make a concentrate which can be diluted or whether the composition constitutes the formulation of the end product detergent.

The other main component of the compositions of the present invention is a water-soluble salt of an aryl, aralkyl or alkyl polyalkylene ether sulfate. The ES salts of the present invention have the general formula $$[R-(A)_nO-SO_3]_xM$$

wherein R is a hydrocarbon group containing from about 4 to about 30 carbon atoms, A is an oxyalkylene group selected from the group consisting of oxyethylene, oxypropylene, oxybutylene, oxytetramethylene and heteric and block mixtures thereof, n is an integer from 1 to 8 and M is a cation of a water-soluble salt, and wherein when the average value of n is from 1 to 8, at least about 85% by weight of said ether sulfate has a number average oxyalkylene number of $p-2$ to $p+3$, wherein p represents the number of oxyalkyene groups of the most prevalent oxyalkylate species, and x is 1 or 2 depending on the valence of M. The value of 85% by weight is based on the ES salt being substantially free of unreacted alcohol from which the R group is derived.

The R group may be aryl or aralkyl, but is usually an alkyl group which may be straight chain or branched chain, saturated or unsaturated. Especially preferred ES salts are those wherein the R group is alkyl and contains from about 8 to about 18 carbon atoms, especially from about 8 to about 14 carbon atoms and wherein the oxyalkylene group is oxyethylene and the average of n is from about 1 to about 6, particularly from about 1 to about 4. While M can be a mono or divalent cation, in the preferred case, M is ammonium or a monovalent metal, especially an alkali metal, most preferably sodium.

The ES salts will be present in the surfactant composition in amounts ranging from about 5 to about 30% by weight, especially from about 10 to about 20% by weight.

As noted above, it is known that neutral salts will thicken or viscosify aqueous ES salt compositions. The finding of the present invention is that if the ES salt is of a type where the oxyalkylene groups are "peaked," less neutral salt thixotrope is required to achieve the desired viscosity. Moreover, using such peaked ES salt compositions, there is an increase in the maximum viscosity that can be reached. The net result is that less neutral salt is required to achieve the desired rheological properties. The term "peaked," as used herein, refers to an ES salt wherein the molecular weight distribution of the alkoxylates is narrower than conventional distributions. Applicants have unexpectedly found that by using the ES salts of alkoxylated alcohols having a peaked or narrow distribution with respect to the oxyalkylene group, viscosified surfactant compositions can be obtained using less neutral salt thixotrope than would be required with prior art ES salts having a broader or less peaked distribution.

In order to achieve suitable viscosified compositions with minimal neutral salt thixotrope, at least about 85% by weight of the ES salt, when the ES salt has an average of about 8 or less oxyalkylene group, should have a number average oxyalkylene number of from $p-2$ to $p+3$, wherein p represents the number of oxyalkylene groups of the most prevalent oxyalkylate species. For example, if the average peak number of oxyalkylene group, i.e. group A is 2, then 85% by weight of the ES salt would have oxyalkylene groups ranging from 1 to 5.

It has been found that in conventional, less peaked ES salts of alkoxylated alcohols, when the average of n is less than about 8, generally less than 80% of the ES salt has a number average oxyalkylene number of $p-2$ to $p+3$.

Table I below gives a comparison of the distribution oxyethylene groups of a peaked ES salt useful in the compositions of the present invention with a conventional, "unpeaked" prior art ES salt. In Table I, the calculated values are for ES salts which are substantially free of any unreacted alcohol used as a starting material in the initial alkoxylation reaction. In all cases, the ES salts were derived from a $C_{12}$ straight chain alcohol, i.e. R is $C_{12}$. Samples 1, 3, 5 and 7 are ES salts of the prior art, conventional type having a generally broader distribution of oxyethylene groups, while Samples 2, 4 and 6 are comparable ES salts of the peaked variety useful in compositions of the present invention. Table I also shows the weight percent of ES salt for each of the samples which has a number average oxyethylene number of from $p-2$ to $p+3$. Table I also shows the average number of moles EO for each of the samples.

TABLE I

| | Sample No. | | | |
|---|---|---|---|---|
| Moles EO | 1 | 2 | 3 | 4 |
| 0 | 0 | 0 | 0 | 0 |
| 1 | 33.47 | 34.12 | 21.70 | 19.27 |
| 2 | 21.16 | 30.24 | 17.22 | 20.34 |
| 3 | 15.97 | 22.77 | 15.72 | 27.22 |
| 4 | 10.31 | 9.30 | 12.36 | 20.33 |
| 5 | 6.52 | 2.60 | 8.99 | 9.01 |
| 6 | 4.53 | 0.61 | 7.03 | 2.81 |
| 7 | 3.16 | 0.19 | 5.46 | 0.71 |
| 8 | 2.07 | 0.10 | 4.00 | 0.18 |
| 9 | 1.25 | 0.04 | 2.79 | 0.07 |
| 10 | 0.75 | 0.03 | 1.86 | 0.04 |
| 11 | 0.42 | | 1.17 | 0.02 |
| 12 | 0.22 | | 0.71 | |
| 13 | 0.11 | | 0.40 | |
| 14 | 0.06 | | 0.22 | |
| 15 | | | 0.11 | |
| 16 | | | 0.07 | |
| 17 | | | 0.03 | |
| 18 | | | 0.17 | |
| 19 | | | | |
| 20 | | | | |
| 21 | | | | |
| Wt % ($p-2 \rightarrow p+3$) | 80.91 | 96.43 | 67.00 | 98.99 |
| Average Moles EO | 2.41 | 2.0 | 3.13 | 2.65 |

TABLE I-continued

| | Sample No. | | | |
|---|---|---|---|---|
| | 5 | 6 | 7 | 8 |
| 0 | 0 | 0 | 0 | 0 |
| 1 | 13.19 | 8.83 | 2.98 | 0.38 |
| 2 | 13.56 | 14.96 | 4.01 | 0.85 |
| 3 | 13.57 | 23.17 | 5.28 | 2.25 |
| 4 | 12.21 | 23.17 | 5.28 | 2.25 |
| 5 | 10.10 | 16.75 | 6.84 | 12.15 |
| 6 | 8.73 | 8.17 | 7.69 | 18.74 |
| 7 | 7.46 | 2.88 | 8.36 | 21.49 |
| 8 | 6.09 | 0.80 | 8.71 | 18.03 |
| 9 | 4.69 | 0.22 | 8.51 | 11.41 |
| 10 | 3.49 | 0.07 | 8.09 | 5.64 |
| 11 | 2.47 | | 7.28 | 2.23 |
| 12 | 1.68 | | 6.32 | 0.75 |
| 13 | 1.11 | | 5.27 | 0.21 |
| 14 | 0.71 | | 4.22 | 0.04 |
| 15 | 0.45 | | 3.32 | |
| 16 | 0.25 | | 2.50 | |
| 17 | 0.14 | | 1.81 | |
| 18 | 0.08 | | 1.17 | |
| 19 | 0.04 | | 0.70 | |
| 20 | 0.00 | | 0.40 | |
| 21 | | | 0.22 | |
| Wt % ($p-2 \rightarrow p+3$) | 71.35 | 90.08 | 48.64 | 87.46 |
| Average Moles EO | 3.98 | 3.35 | 7.17 | 6.60 |

As can be seen from Table I, the ES salts which are useful in the compositions of the present invention, and when the number of EO groups is 8 or less, have a number average oxyethylene number of from $p-2$ top $+3$ which constitutes at least about 85% by weight of the ES salt.

EXAMPLE 1

A series of samples containing water, varying amounts of sodium chloride and 15% by weight (active) ES salt were prepared and the viscosity measured. In all cases, the viscosity was measured at 25° C. at a shear rate of 7.5 $sec^{-1}$. The results are shown in Table II below, together with a comparison of the average moles of EO versus the weight percent of the ES salt having a number average oxyethylene number of $p-2$ to $p+3$.

TABLE II

| NaCl (Wt. %) Sample[1] | Viscosity vs. Salt Concentration (cP) 0 | 1 | 3 | 5 | 7 | 9 | Av. Moles EO | p − 2-p + 3 (Wt. %) |
|---|---|---|---|---|---|---|---|---|
| A | | | 19.6 | 8300 | 8300 | 340 | 2.41 | 80.91 |
| B | 0 | 19.6 | 0 | 614 | 7900 | 8100 | 3.98 | 71.35 |
| C | 19.6 | 0 | 0 | 0 | 19.6 | 157 | 4.52 | 67.92 |
| D | 0 | 0 | 0 | 0 | 0 | 0 | 7.17 | 48.64 |
| E | | 0 | 14,500 | 33,600 | 1570 | 360 | 2.0 | 96.43 |
| F | 19.6 | 19.6 | 39.2 | 6480 | 28200 | 8750 | 3.35 | 90.08 |
| G | | 6 | 8 | 0 | 14.8 | 72 | 4.25 | 87.86 |
| H | 19.6 | 0 | 0 | 0 | 13.1 | 0 | 6.60 | 87.46 |

[1]All ES salt samples hd a $C_{12}$ branched chain R group.

Samples A, B, C and D are ES salts of conventional alkoxylate derivatives, whereas Samples E, F, G and H are ES salts of peaked alkoxylate derivatives having a narrower distribution. As can be seen, by comparing, for example, Sample A with Sample E, use of the peaked ES salts results in an unexpectedly large viscosification effect. Whereas 5% sodium chloride with the conventional ES salt (Sample A) results in a viscosity of 8300 cP, the same amount of sodium chloride with a peaked ES salt (Sample E) in a viscosity of 32,600 cP. Similar results can be seen from comparing Samples B (conventional) and F (peaked). It is clear that for a given amount of a neutral salt thixotrope, the maximum viscosity which can be achieved by using the peaked ES salt is much greater than what can be achieved using conventional ES salts having a broader distribution. Not only does the use of the peaked ES salts increase the maximum viscosity which can be achieved, the use of such peaked ES salts permits far less neutral salt thixotrope to be used. For example, by comparing Sample A with Sample E, it will be apparent that in order to achieve the viscosity achieved in Sample A containing 5% sodium chloride, Sample E would only have to contain 2–3% sodium chloride.

The surfactant compositions of the present invention can be used in formulating end product detergents, such as shampoos, liquid hand soaps, etc. It will be apparent that other ingredients commonly incorporated into such detergents can be employed. Such ingredients include, without limitation, builders, perfumes, conditioning agents, etc.

The foregoing disclosure and description of the invention is illustrative and explanatory thereof, and various changes in the size, shape and materials as well as in the details of the illustrated construction may be made within the scope of the appended claims without departing from the spirit of the invention.

What is claimed is:

1. A composition for use in formulating detergents comprising:
   water;
   a viscosity imparting amount of a neutral salt thixotrope; and
   an effective amount of a water-soluble salt of an ether sulfate having the formula $$[R-(A)_nO-SO_3]_xM$$

wherein R is a hydrocarbon group containing from about 4 to about 30 carbon atoms, A is an oxyalkylene group selected from oxyethylene, oxypropylene, oxybutylene, oxytetramethylene and heteric and block mixtures thereof, n is an integer from 1 to 8 and M is a cation of a water-soluble salt, and wherein when the average of n is from 1 to 8, at least about 85% by weight of said ether sulfate has a number average oxyalkylene number of $p-2$ to $p+3$, wherein p represents the number of oxyalkyene groups of the most prevalent oxyalkylate species, and x is 1 or 2 depending on the valence of M.

2. The composition of claim 1 wherein R contains from about 8 to about 18 carbon atoms.

3. The composition of claim 1 wherein the average of n is from about 1 to about 6.

4. The composition of claim 1 wherein M is sodium.

5. The composition of claim 1 wherein said neutral salt thixotrope is selected from the class consisting of alkaline metal halides, alkaline metal sulfates, ammonium halides, ammonium sulfates and mixtures thereof.

6. The composition of claim 1 wherein said neutral salt thixotrope is present in an amount of from about 1 to about 10% by weight.

7. The composition of claim 1 wherein said salt of said ether sulfate is present in an amount of from about 5 to about 30% by weight.

* * * * *